US012570696B2

(12) United States Patent
Li et al.

(10) Patent No.: US 12,570,696 B2
(45) Date of Patent: Mar. 10, 2026

(54) TUMOR-SPECIFIC POLYPEPTIDE SEQUENCE AND USE THEREOF

(71) Applicant: SHENZHEN GINO BIOTECHNOLOGY CO., LTD., Shenzhen (CN)

(72) Inventors: Bo Li, Shenzhen (CN); Si Qiu, Shenzhen (CN); Youping Li, Shenzhen (CN); Le Zhang, Shenzhen (CN)

(73) Assignee: SHENZHEN GINO BIOTECHNOLOGY CO., LTD., Shenzhen (CN)

( * ) Notice: Subject to any disclaimer, the term of this patent is extended or adjusted under 35 U.S.C. 154(b) by 921 days.

(21) Appl. No.: 17/774,873

(22) PCT Filed: Nov. 7, 2019

(86) PCT No.: PCT/CN2019/116163
§ 371 (c)(1),
(2) Date: May 6, 2022

(87) PCT Pub. No.: WO2021/087838
PCT Pub. Date: May 14, 2021

(65) Prior Publication Data
US 2023/0059675 A1      Feb. 23, 2023

(51) Int. Cl.
| | |
|---|---|
| *C07K 7/08* | (2006.01) |
| *A61K 39/395* | (2006.01) |
| *A61K 40/19* | (2025.01) |
| *A61K 40/24* | (2025.01) |
| *A61K 40/42* | (2025.01) |
| *C12N 15/63* | (2006.01) |
| *A61K 39/00* | (2006.01) |

(52) U.S. Cl.
CPC .......... *C07K 7/08* (2013.01); *A61K 39/39558* (2013.01); *A61K 40/19* (2025.01); *A61K 40/24* (2025.01); *A61K 40/42* (2025.01); *C12N 15/63* (2013.01); *A61K 2039/6031* (2013.01); *A61K 2239/31* (2023.05); *A61K 2239/38* (2023.05)

(58) Field of Classification Search
CPC ..... C07K 7/08; A61K 39/39558; C12N 15/63
See application file for complete search history.

(56) References Cited

U.S. PATENT DOCUMENTS

| | | | |
|---|---|---|---|
| 2018/0153975 A1* | 6/2018 | Fritsch | .......... A61K 39/001152 |
| 2019/0290686 A1 | 9/2019 | Wickham et al. | |

FOREIGN PATENT DOCUMENTS

| | | | |
|---|---|---|---|
| CN | 101688243 A | 3/2010 | |
| CN | 108434440 A | 8/2018 | |
| CN | 109069604 A | 12/2018 | |
| CN | 109310739 A | 2/2019 | |
| TW | 201930340 A | 8/2019 | |
| WO | 2013036201 A1 | 3/2013 | |
| WO | WO-2016164833 A1 * | 10/2016 | .......... C12N 5/0693 |
| WO | WO-2017147139 A1 * | 8/2017 | ......... A61K 39/0011 |
| WO | WO-2017173321 A1 * | 10/2017 | .............. C07K 4/12 |

OTHER PUBLICATIONS

Filip Janku et al., "PIK3CA Mutation H1047R Is Associated with Response to PI3K/AKT/mTOR Signaling Pathway Inhibitors in Early-Phase Clinical Trials", Cancer Research, 73(1), Jan. 1, 2013, pp. 276-284, doi: 10.1158/0008-5472.CAN-12-1726.
Translated TW Office Action; Application No. 109105412; Dated Mar. 31, 2021, Entire document.
Translated TW Search Report; Application No. 109105412; Dated Mar. 16, 2021, Entire document.
Extended European Search Report, Application No. 19951972.9-1111, dated Aug. 25, 2023, pp. 1-7.

* cited by examiner

*Primary Examiner* — Amber D Steele
(74) *Attorney, Agent, or Firm* — BOND, SCHOENECK & KING, PLLC; George R. McGuire

(57) ABSTRACT
Provided are a tumor-specific polypeptide sequence and use thereof. The polypeptide includes at least one polypeptide in a first peptide group, and optionally, at least one polypeptide in a second peptide group, the first peptide group includes polypeptides having amino acid sequences set forth in SEQ ID NO: 1 to SEQ ID NO: 4, the second peptide group includes derivative peptides of the amino acid sequences set forth in SEQ ID NO: 1 to SEQ ID NO: 4, the derivative peptide includes a front peptide segment, a middle peptide segment, and a back peptide segment that are connected in sequence. Further provided are a nucleic acid, a construct, an expression vector, a pharmaceutical composition, an antigen-presenting cell, an immune effector cell, a tumor vaccine, use of the polypeptide in the preparation of drugs for preventing or treating tumors, and a method for treating a patient suffering from tumors.

12 Claims, 5 Drawing Sheets

Specification includes a Sequence Listing.

RHGGWTTK                                            Control

Days

— ⊕ — Adjuvant + blank polypeptide group
— ◆ — Adjuvant +wild-type polypeptide HHGGWTTK group
— ⊙ — Adjuvant + mutant polypeptide RHGGWTTK group
— ▲ — Adjuvant + variant polypeptide RAGGWTTK group
— ⊗ — Adjuvant + variant polypeptide RSGGWTTK group
— ⊛ — Adjuvant + variant polypeptide RVGGWTTK group Days ——◆— Blank polypeptide-loaded DC group ··■·· Wild-type polypeptide HHGGWTTK-loaded DC group ——▲— Mutant polypeptide RHGGWTTK-loaded DC group ———— Variant polypeptide RAGGWTTK-loaded DC group ———— Variant polypeptide RSGGWTTK-loaded DC group ——●— Variant polypeptide RVGGWTTK-loaded DC group Days ——◆—— Blank polypeptide-loaded DC + CTL group ——■——Wild-type polypeptide HHGGWTTK-loaded DC+ CTL group ——⬣—— Mutant polypeptide RHGGWTTK-loaded DC+ CTL group —-✳-— Variant polypeptide RAGGWTTK-loaded DC+ CTL group —-✳-— Variant polypeptide RSGGWTTK-loaded DC+ CTL group ——◆—— Variant polypeptide RVGGWTTK-loaded DC+ CTL group

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: Variant polypeptide

<400> SEQUENCE: 1

Arg Ala Gly Gly Trp Thr Thr Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Mutant polypeptide
```

-continued

```
<400> SEQUENCE: 2

Arg His Gly Gly Trp Thr Thr Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Variant polypeptide

<400> SEQUENCE: 3

Arg Ser Gly Gly Trp Thr Thr Lys
1               5

<210> SEQ ID NO 4
<211> LENGTH: 8
<212> TYPE: PRT
<213> ORGANISM: Artificial sequence
<220> FEATURE:
<223> OTHER INFORMATION: Variant polypeptide

<400> SEQUENCE: 4

Arg Val Gly Gly Trp Thr Thr Lys
1               5

<210> SEQ ID NO 5
<211> LENGTH: 26
<212> TYPE: PRT
<213> ORGANISM: Artificial sequence
<220> FEATURE:
<223> OTHER INFORMATION: Derivative peptide

<400> SEQUENCE: 5

Glu Ala Leu Glu Tyr Phe Met Lys Gln Met Asn Asp Ala Arg Ala Gly
1               5                   10                  15

Gly Trp Thr Thr Lys Met Asp Trp Ile Phe
            20                  25

<210> SEQ ID NO 6
<211> LENGTH: 26
<212> TYPE: PRT
<213> ORGANISM: Artificial sequence
<220> FEATURE:
<223> OTHER INFORMATION: Derivative peptide

<400> SEQUENCE: 6

Glu Ala Leu Glu Tyr Phe Met Lys Gln Met Asn Asp Ala Arg His Gly
1               5                   10                  15

Gly Trp Thr Thr Lys Met Asp Trp Ile Phe
            20                  25

<210> SEQ ID NO 7
<211> LENGTH: 26
<212> TYPE: PRT
<213> ORGANISM: Artificial Sequence
<220> FEATURE:
<223> OTHER INFORMATION: Derivative peptide

<400> SEQUENCE: 7

Glu Ala Leu Glu Tyr Phe Met Lys Gln Met Asn Asp Ala Arg Ser Gly
1               5                   10                  15

Gly Trp Thr Thr Lys Met Asp Trp Ile Phe
            20                  25
```

-continued

```
<210> SEQ ID NO 8
<211> LENGTH: 26
<212> TYPE: PRT
<213> ORGANISM: Artificial Sequence
<220> FEATURE:
<223> OTHER INFORMATION: Derivative peptide

<400> SEQUENCE: 8

Glu Ala Leu Glu Tyr Phe Met Lys Gln Met Asn Asp Ala Arg Val Gly
1               5                   10                  15

Gly Trp Thr Thr Lys Met Asp Trp Ile Phe
            20                  25

<210> SEQ ID NO 9
<211> LENGTH: 9
<212> TYPE: PRT
<213> ORGANISM: Artificial Sequence
<220> FEATURE:
<223> OTHER INFORMATION: CMV polypeptide

<400> SEQUENCE: 9

Asn Leu Val Pro Met Val Ala Thr Val
1               5

<210> SEQ ID NO 10
<211> LENGTH: 8
<212> TYPE: PRT
<213> ORGANISM: Artificial Sequence
<220> FEATURE:
<223> OTHER INFORMATION: Wild-type polypeptide

<400> SEQUENCE: 10

His His Gly Gly Trp Thr Thr Lys
1               5
```

TUMOR-SPECIFIC POLYPEPTIDE SEQUENCE AND USE THEREOF

FIELD

The present disclosure relates to the field of biomedicine, and particularly, to tumor-specific polypeptide sequences and uses thereof. In particular, the present disclosure relates to an isolated polypeptide group, an isolated nucleic acid, a construct, an expression vector, a host cell, a pharmaceutical composition, an antigen-presenting cell, an immune effector cell, a tumor vaccine, use of the polypeptide in the preparation of drugs for preventing or treating tumors, and a method for treating a patient suffering from tumors.

BACKGROUND

Cancer, as a disease of uncontrolled cell proliferation caused by gene mutations in cells, has become a major threat to human health and is a major cause of human death. According to the "Analysis of the Epidemiology of Malignant Tumors in China in 2015" issued by the National Cancer Center, there were about 3.929 million malignant tumor incidences and 2.338 million malignant tumor deaths in China in 2015. The burden of cancer continues to rise. In the past 10 years, the incidence of malignant tumors has maintained an annual increase of about 3.9%, and the mortality rate has maintained an annual increase of 2.5%. Among them, the main high-incidence malignant tumors are lung cancer, gastric cancer, colorectal cancer, liver cancer, breast cancer and esophageal cancer. Therefore, it is of great clinical value to find efficient and specific cancer treatment methods.

Immunotherapy, by modulating the body's immune system, enhances the anti-tumor immunity of tumor microenvironment, so as to achieve the purpose of controlling and killing tumor cells. The immunotherapy has the advantages of high efficiency, high specificity, and good tolerance, and thus it has broad application prospect in tumor treatment.

The immunotherapy mainly includes cytokine therapy, immune checkpoint monoclonal antibodies, adoptive cell reinfusion, and tumor immunotherapy vaccines, etc. Among them, the tumor immunotherapy vaccines mainly include tumor cell vaccines, dendritic cell vaccines, protein & polypeptide vaccines, nucleic acid vaccines, genetic engineering vaccines and anti-idiotype antibody vaccines. The main mechanism of these vaccines killing tumors is causing patients' immune response against tumors, thereby allowing T cells to recognize tumor cells and kill tumor cells.

Tumor antigens targeted by the tumor immunotherapy vaccines include tumor-associated antigens and tumor neoantigens. The tumor-associated antigens are derived from proteins that are highly expressed in tumor tissues but are low-expressed or not expressed in normal tissues. The tumor neoantigens are derived from mutant proteins produced by mutations in the tumor genome. As the tumor neoantigens only exist in tumor cells and do not exist in normal cells, the neoantigens can bypass the central immunotolerance and cause a strong T cell immune response, which has the characteristics of good effect. Meanwhile, the tumor neoantigens, due to the characteristics of tumor specificity, have the advantages of good safety and insignificant side effects. However, it is still necessary to further improve the tumor neoantigens targeted by suitable tumor immunotherapy vaccines.

SUMMARY

The present disclosure provides aims to solve one of the technical problems in the related art at least to a certain extent. To this end, an object of the present disclosure is to provide a tumor-specific polypeptide sequence and use thereof, specifically related to an isolated polypeptide group, an isolated nucleic acid, a construct, an expression vector, a host cell, a pharmaceutical composition, an antigen-presenting cell, an immune effector cell, a tumor vaccine, use of the polypeptide in the preparation of drugs for preventing or treating tumors, and a method for treating a patient suffering from tumors.

Several schemes are usually adopted to perform a tumor immunotherapy on patients. Scheme 1: treating the patient by using tumor-associated antigens that are highly expressed in the patient's tumor. Such a treatment method may have poor effects, as the tumor-associated antigens may also be expressed in some normal tissues and thus these tumor-associated antigens may have low immunogenicity. Scheme 2: treating the patient by using tumor-associated antigens or tumor neoantigens that have been experimentally identified in some patients. However, tumor mutations are patient-specific, and most of the tumor mutations will not be repeated in multiple patients. Therefore, if the tumor-specific antigens identified in some patients have not been verified for their frequency of occurrence in a large number of tumor patients, the probability of re-use in new patients is low, and thus the number of patients who can be treated with these tumor neoantigens is small. Scheme 3: performing individualized tumor neoantigen screening for each patient. For example, the tumor-specific mutations of the patient and the variant peptide segments that may be generated by these mutations can be obtained by analyzing the sequencing data of the patient's genome and transcriptome, then the machine learning algorithm can be employed to predict which variant peptide segments may be presented by MHC molecules to become antigens, and then these predicted tumor neoantigens are used for patient treatment. Regarding the individualized tumor neoantigen screening scheme based on sequencing, although genome and transcriptome of a certain patient can be sequenced and the tumor neoantigens for treating the specific patient can be screened out through the sequencing data analysis and antigen algorithm prediction, the whole process is costly and time-consuming, the screened antigens have a high false positive rate due to the low accuracy of the existing antigen prediction algorithm, and some of the predicted antigens cannot effectively cause an immune response in the patient's body, thereby leading to a poor curative effect for the patient. Scheme 4: combining the above schemes, that is, using a group of identified tumor-associated antigens and tumor neoantigens, in combination with the individualized tumor neoantigen screening program. For example, the antigens known in Scheme 1 or Scheme 2 are used to perform a first stage of treatment on the patient, and at the same time, the individualized antigen screening is performed on the patient with reference to Scheme 3, and then the antigens obtained from the screening are used to perform a second stage of treatment on the patient. Although such a scheme can solve the long-time consuming problem of individualized tumor neoantigen screening, the treatment cost still cannot be lowered due to the involvement of the scheme of individualized tumor neoantigen screening.

Through a large amount of data analysis and experimental screening, the present disclosure has discovered the high-frequency mutant gene PIK3CA (a catalytic subunit of wild-type PIK3CA gene, PI3Ks, which are a kind of lipid kinase family and can specifically phosphorylate 3-position hydroxy of phosphatidylinositol to generate second messenger inositol materials) that appear repeatedly in a variety of cancers. This high-frequency mutant gene causes its amino acid encoding position 1047 to be changed from histidine (H) to arginine (R). The mutant polypeptide can be specifically and highly expressed in tumor tissues. In the present disclosure, the high affinity of the mutant polypeptide with HLA-A11: 01 subtype molecules and the presentation in tumor cells have been verified through experiments. Furthermore, the present disclosure modifies the sequence of the mutant polypeptide, and has screened out, through a large number of experiments, variant polypeptides that can be recognized by the same T cells like the original mutant polypeptide but have a better ability of activating T cells and inducing antigen-specific T cells to kill tumors.

Specifically, the present disclosure provides the following technical solutions.

In a first aspect of the present disclosure, the present disclosure provides a group of isolated polypeptides. The isolated polypeptide group includes at least one polypeptide in a first peptide group, and optionally, at least one polypeptide in a second peptide group. The first peptide group includes polypeptides having amino acid sequences set forth in SEQ ID NO: 1 to SEQ ID NO: 4. The second peptide group includes derivative peptides of the amino acid sequences set forth in SEQ ID NO: 1 to SEQ ID NO: 4. The derivative peptides each include a front peptide segment, a middle peptide segment, and a back peptide segment that are connected in sequence. The middle peptide segment has at least 80% homology with the amino acid sequences set forth in SEQ ID NO: 1 to SEQ ID NO: 4. A sum of lengths of the front peptide segment and the back peptide segment ranges from 17 to 19 amino acids.

The above polypeptide sequences, as tumor neoantigen polypeptide sequences, are tumor-specific antigens produced by the tumor gene mutations and variants thereof, and they will not be expressed and presented in the normal tissues, thereby solving the problem of low safety when using tumor-associated antigens. Meanwhile, the polypeptide sequences provided by the present disclosure are derived from the high-frequency mutant genes in various cancers, and can be presented by HLA molecules that frequently appear in the population, such that they can repeatedly appear in the tumors of patients with various cancers, thereby covering the patients that cannot be covered by currently known tumor neoantigen sequences.

According to the embodiments of the present disclosure, the isolated polypeptides as described above may further have the following technical features.

In some embodiments of the present disclosure, the middle peptide segment has an amino acid sequence as set forth in SEQ ID NO: 1 to SEQ ID NO: 4.

In some embodiments of the present disclosure, the derivative peptides have amino acid sequences set forth in SEQ ID NO: 5 to SEQ ID NO: 8.

In some embodiments of the present disclosure, a polypeptide of the isolated polypeptide group is selected from at least one group of:

group 1: at least two polypeptides having amino acid sequences set forth in SEQ ID NO: 1 to SEQ ID NO: 4; or group 2: at least one polypeptide having an amino acid sequence set forth in SEQ ID NO: 1 to SEQ ID NO: 4, and at least one polypeptide having an amino acid sequence set forth in SEQ ID NO: 5 to SEQ ID NO: 8.

In a second aspect of the present disclosure, the present disclosure provides an isolated nucleic acid or a complementary sequence thereof. According to the embodiments of the present disclosure, the nucleic acid encodes a polypeptide selected from the isolated polypeptide group as described above. As described above, the above-mentioned polypeptides, as antigens, can be presented on the surface of tumor cells by HLA molecules having affinity with these polypeptides, and these polypeptides have the ability of activating T cells and directing these T cells to kill tumors. Thus, the nucleic acid sequences capable of encoding the above-mentioned polypeptides, or the sequences complementary to these nucleic acid sequences capable of encoding the above-mentioned polypeptides can be used to prevent or treat tumors.

In a third aspect of the present disclosure, the present disclosure provides a construct. According to the embodiments of the present disclosure, the construct includes the nucleic acid according to the second aspect of the present disclosure, and a control sequence. The control sequence is operably linked to the encoding sequence. The construct provided by the embodiments of the present disclosure can efficiently express the above-mentioned polypeptides in suitable host cells under appropriate conditions, and thus the construct can be effectively used for the treatment or prevention of tumors. The control sequence can direct the nucleic acid to express the above-mentioned polypeptides in the hosts, and one or more control sequences may be included. These control sequences may be promoters, terminators, SD sequences, regulatory genes for regulating the gene expression, and the like, as required.

In a fourth aspect of the present disclosure, the present disclosure provides an expression vector. According to the embodiments of the present disclosure, the expression vector includes the construct according to the third aspect of the present disclosure. The expression vector provided by the embodiments of the present disclosure can efficiently express the above-mentioned polypeptides in hosts under suitable conditions, and the expression vector can be effectively used for the treatment or prevention of tumors.

In a fifth aspect of the present disclosure, the present disclosure provides a host cell. According to the embodiments of the present disclosure, the host cell carries the construct according to the third aspect of the present disclosure or the expression vector according to the fourth aspect of the present disclosure. The host cells can be obtained through a transfection or transformation of the aforementioned nucleic acid construct or expression vector. The host cells can efficiently express the above-mentioned polypeptides under suitable conditions, and the host cells can be effectively used for the treatment or prevention of tumors.

In a sixth aspect of the present disclosure, the present disclosure provides use of a polypeptide selected from the isolated polypeptide group as described above in the preparation of drugs for preventing or treating tumors or in the preparation of kits for diagnosing tumors. If the tumor expresses the above-mentioned mutant gene PIK3CA, this high-frequency mutant gene causing its amino acid encoding position 1047 to be changed from histidine (H) to arginine (R) and expresses HLA molecules with affinity with the polypeptides, according to the embodiments of the present disclosure, the above-mentioned polypeptides can be presented on the surface of tumor cells as antigens by HLA molecules having affinity with the polypeptides, so as to activate and direct T cells to kill tumors. Therefore, the polypeptides proposed in the embodiments of the present invention can be used to prevent and control tumors. At the same time, as mentioned above, since the polypeptides provided by the present disclosure are specifically expressed in the tumor cells, they are safer to treat or prevent tumors. They can also be used in the preparation of kits for diagnosing tumors.

In a seventh aspect of the present disclosure, the present disclosure provides a pharmaceutical composition. According to the embodiments of the present disclosure, the pharmaceutical composition includes a polypeptide selected from the isolated polypeptide group and a pharmaceutically acceptable excipient. The pharmaceutical composition including the above-mentioned polypeptides and the excipient can significantly stimulate the proliferation of tumor-specific T cells and the cytokine secretion of these T cells to kill the tumor cells expressing the corresponding mutant genes, and thus can be used in the treatment or prevention of tumors. The above pharmaceutical composition may also include some pharmaceutically acceptable adjuvants. These adjuvants, as non-specific immune enhancers, can enhance the body's immune response to polypeptide antigens or change the type of immune response, when they are injected together with the aforementioned polypeptides or pre-injected into the body. The suitable adjuvants include, but are not limited to, PD-1 inhibitors.

In an eight aspect of the present disclosure, the present disclosure provides an antigen-presenting cell. According to the embodiments of the present disclosure, the antigen-presenting cell is capable of presenting a polypeptide selected from the isolated polypeptide group. The antigen-presenting cell can be obtained by loading the polypeptide, transfecting or transforming the aforementioned nucleic acid construct or expression vector, or phagocytosing the aforementioned host cell. According to the embodiments of the present disclosure, the antigen-presenting cells presenting the aforementioned polypeptides significantly stimulate the proliferation of tumor-specific T cells and the cytokine secretion of these T cells, thereby killing tumor cells expressing the corresponding mutant genes, and thus the antigen-presenting cells can be used for the treatment or prevention of tumors. These usable antigen-presenting cells can be dendritic cells, macrophages, B cells, and the like.

In a ninth aspect of the present disclosure, the present disclosure provides an immune effector cell. According to the embodiments of the present disclosure, the immune effector cell is capable of recognizing a polypeptide selected from the isolated polypeptide group or the antigen-presenting cell according to the eighth aspect of the present disclosure. The immune effector cell can be obtained through inducing of the above-mentioned polypeptides or the above-mentioned antigen-presenting cells. These immune effector cells can specifically kill tumor cells expressing the corresponding mutant genes, and thus can be used for the treatment or prevention of tumors. The usable immune effector cells can be T cells, effector T cells, NK cells and the like.

In a tenth aspect of the present disclosure, the present disclosure provides a tumor vaccine. According to the embodiments of the present disclosure, the tumor vaccine includes the nucleic acid as described above, or the nucleic acid construct as described above, or the expression vector as described above, or the host cell as described above, or the antigen-presenting cell as described above, or the immune effector cell as described above.

In an eleventh aspect of the present disclosure, the present disclosure provides a method for treating a patient suffering from tumors. The method includes: administering an effective amount of the pharmaceutical composition as described in the seventh aspect or an effective amount of the tumor vaccine as described in the tenth aspect to the patient. The "effective amount" of the pharmaceutical composition refers to an amount that can achieve the purpose of inhibiting tumor growth or intervening tumor proliferation. The "effective amount" of the tumor vaccine refers to an amount of the tumor vaccine which, once introduced to patient's body, can overcome the immunosuppressive state caused by tumors and activate the patient's own immune system once being introduced to patient's body, thereby controlling or eliminating the tumors.

DESCRIPTION OF EMBODIMENTS

Figure 1:
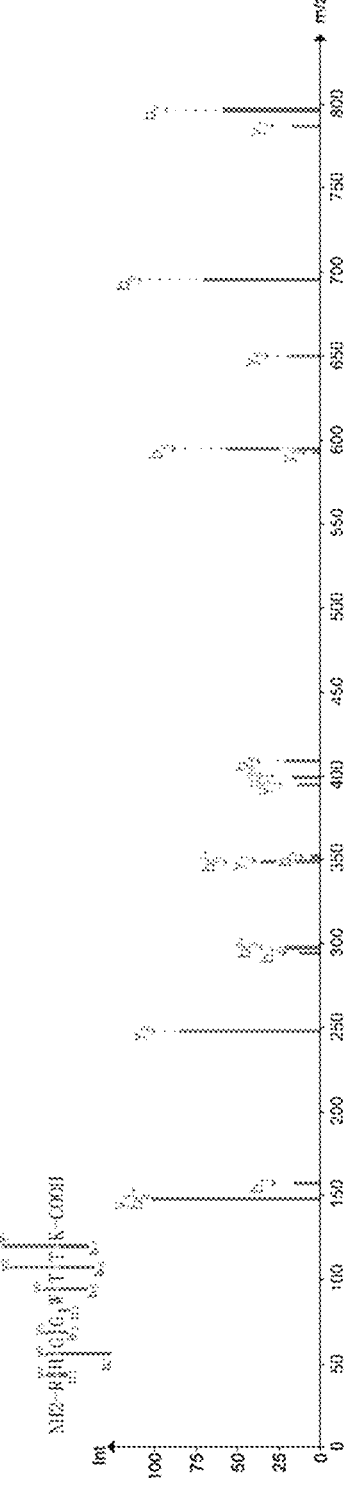
FIG. 1 illustrates a result diagram of mass spectrometry identification of a mutant polypeptide (SEQ ID NO: 2) according to embodiments of the present disclosure.

The embodiments of the present disclosure will be described in detail below with reference to the accompanying drawings. It should be noted that these embodiments are exemplary and are intended to be used to explain the present disclosure, rather than being construed as limitations on the present disclosure.

Meanwhile, some terms of the present disclosure are explained and described in order to facilitate the understanding of those skilled in the art. It should be noted that these explanations and descriptions are only used to help the understanding of the technical solutions of the present disclosure, and should not be considered as limitations on the scope of protection of the present disclosure.

Terms "first peptide group" or "second peptide group" refer to polypeptides containing different amino acid sequences.

Term "derivative peptides" are used to represent polypeptide sequences derived from polypeptides having amino acid sequences set forth in SEQ ID NO: 1 to SEQ ID NO: 4. The sequence of each of these derivative peptides includes, from the N-terminus to the C-terminus, a front peptide segment, a middle peptide segment, and a back peptide segment that are connected in sequence. The middle peptide segment has at least 80% homology with the amino acid sequences set forth in SEQ ID NO: 1 to SEQ ID NO: 4, for example, having at least one different amino acid. A sum of lengths of the front peptide segment and the back peptide segment ranges from 17 amino acids to 19 amino acids. The specific types of amino acids of the front peptide segment and the back peptide segment may not be particularly limited. In at least some embodiments, these derivative peptides may be long peptide sequences obtained by extending the amino acid sequences set forth in SEQ ID NO: 1 to SEQ ID NO: 4 from both ends to a total length of 26 amino acids. In some preferred embodiments, these derivative peptides may be polypeptides having the amino acid sequences set forth in SEQ ID NO: 5 to SEQ ID NO: 8.

In at least some embodiments of the present disclosure, a polypeptide of the isolated polypeptide group provided by the present disclosure may be selected from at least one group of: group 1: polypeptides having amino acid sequences set forth in SEQ ID NO: 1 to SEQ ID NO: 4; and group 2: at least one polypeptide having an amino acid sequence set forth in SEQ ID NO: 1 to SEQ ID NO: 4, and at least one polypeptide having an amino acid sequence set forth in SEQ ID NO: 5 to SEQ ID NO: 8.

The polypeptides having the amino acid sequences set forth in SEQ ID NO: 5 to SEQ ID NO: 8 are listed in Table 1.

TABLE 1

Sequences of polypeptides

| SEQ ID | Sequences of poly-peptides | Mutation | SEQ ID | Sequences of derivative peptides |
|---|---|---|---|---|
| NO: 1 | RAGGWTTK | PIK3CA_H1047R | NO: 5 | EALEYFMKQMNDARAGGW TTKMDWIF |
| NO: 2 | RHGGWTTK | PIK3CA_H1047R | NO: 6 | EALEYFMKQMNDARHGGW TTKMDWIF |
| NO: 3 | RSGGWTTK | PIK3CA_H1047R | NO: 7 | EALEYFMKQMNDARSGGW TTKMDWIF |
| NO: 4 | RVGGWTTK | PIK3CA_H1047R | NO: 8 | EALEYFMKQMNDARVGGW TTKMDWIF |

These polypeptide sequences are derived from tumor-specific antigens produced by tumor gene mutations and are not expressed and presented in normal tissues, and thus they are more specific and can cause more specific immune response. Therefore, these polypeptide sequences are safe for the treatment, and have insignificant side effects. In addition, the structures of these polypeptides are simple and easy to be synthesized. Further, the variant sequences provided by the present disclosure are obtained by modifying the original antigen sequences and performing a large number of screening experiments. Compared with the original tumor antigens, they have the affinity with HLA molecules, the ability of stimulating T cells to proliferate and secrete cytokines and the strong ability of inducing antigen-specific T cells to kill target cells, without changing the specificity with T cells, thereby having better tumor control effect.

The schemes of the present disclosure will be explained below in conjunction with the embodiments. Those skilled in the art can understand that the following examples are only used to illustrate the present disclosure and should not be regarded as limiting the scope of the present disclosure. Techniques or conditions, when not specified in the embodiments, shall be those described in the literatures in the related art or shall be in accordance with the product specification. Reagents or instruments, without indicating the manufacturers thereof, shall be conventional and commercially available products.

Example 1

Based on a large amount of tumor mutation data from public database such as TCGA/ICGC, high-frequency mutations were statistically analyzed, the high-frequency typing of the Chinese population was predicted, screened, and experimentally verified to obtain polypeptides. Sequences of the polypeptide are set forth in SEQ ID NO: 1 to SEQ ID NO: 4. Further, the tumor mutation data were also used to obtain the derivative peptides, which are polypeptide sequences obtained by extending the polypeptide sequences from both ends to a total length of 26 amino acids. The derivative peptide sequences are set forth in SEQ ID NO: 5 to SEQ ID NO: 8.

The functions of the respective polypeptide sequences and the respective derivative peptide sequences are studied in following examples. For convenience of description, the sequence set forth in SEQ ID NO: 2 may be referred to as a mutant polypeptide, and the sequences set forth in SEQ ID NO: 1, SEQ ID NO: 3, and SEQ ID NO: 4 may be referred to as variant polypeptides.

Example 2 Verification of Presentation of Polypeptides by HLA Molecules on Surface of Tumor Cells Through Mass Spectrometry Experiments According to the present disclosure, the genes encoding the polypeptides and derivative peptides obtained in Example 1 were transfected into tumor cells by lentiviral transfection, and then the polypeptide-MHC complexes on the cell surface were enriched through the combination of co-immunoprecipitation and mass spectrometry. Then, verification was performed on whether MHC molecules on the surface of tumor cells present the mutant polypeptides. The specific method is described as below.

1. Separation and Purification of MHC-I-Restricted T Cell Epitope Peptides:

Pan-MHC-I A/B/C antibody (clone number: w6/32) were bonded to sepharose CL-4B beads coupled with protein A molecules on the surfaces at 4° C. for 1 hour, and NanoDrop was used to detect the residual antibody content in the supernatant. An antibody binding rate greater than 90% was regarded to be qualified, and pan-MHC-I A/B/C-binding sepharose was prepared and stored at 4° C. for use. 40 ml of RIPA lysate was added to the cell samples, incubated at 4° C. for 1 hour, and centrifuged at 12,000 rpm for 30 min. Then, the sepharose CL-4B beads were added to the supernatant for pre-hybridization, and incubated at 4° C. for 1 hour; the beads were removed by centrifugation, and the pan-MHC-A/B/C-binding sepharose CL-4B beads were added to the supernatant and incubated at 4° C. overnight (16 to 18 hours). The beads were washed three times with PBS pre-cooled at 4° C.; then the beads were washed with ultrapure water; and the washing solution was removed by centrifugation. 0.1N acetic acid was used to elute the antibody-MHC-I protein complexes on the surfaces of the beads, and the antibody-MHC-I protein complexes were dissociated under acidic conditions. Further, proteins and polypeptides in the eluted product were separated and purified using a 3 kDa ultrafiltration tube or c18 solid phase extraction column (25 mg, waters), the purified product was concentrated using a refrigerated vacuum centrifuge, and the concentrated product was stored at −20° C. before being loaded on a mass spectrometer.

2. Mass Spectrometry Identification of MHC-I-Restricted T Cell Epitope Peptides:

A concentrated solution of MHC-I-restricted epitope peptides was analyzed through a Q Exactive mass spectrometer (Thermo Fisher Scientific) online connected to nanoflow HPLC (Thermo Fisher Scientific). A separation column, which was manually filled with ReproSil-Pur C18-AQ 1.9 um for a length of 15 cm and had an inner diameter of 75 um, was used for separation. Buffer B (80% ACN/0.5% acetic acid) of linear gradients from 2% to 30% was used to elute the peptides, with a flow rate of 250 nl/min and an elution time of 90 min. Fragmentation of the secondary mass spectrometry was performed by HCD, and the data-dependent "Top 20" method was selected for data acquisition. The acquisition resolution of the MS spectrum was 70,000, 200 m/z, with a target value of 3E6 ions. The ions having the top 10 ion intensities were usually separated and accumulated with a maximum injection time of 120 ms until the displayed value of the automatic gain controller was 1E5. Polypeptide matching option was set to be "disable", MS/MS resolution was set to be 17,500 (200 m/z).

3. Mass Spectrometry Data Analysis of MHC-I-Restricted T Cell Epitope Peptides:

data analysis was performed using MaxQuant (version 1.3.10.15) to compare mass spectrograms and human whole protein library (Uniprot, 86,749 proteins), tumor-associated antigens, tumor-specific mutant peptide segments, and a list of spectrograms generated from a data set of 247 common contaminants (keratin, bovine serum albumin, and proteases). Variable modification detection setting: N-terminus acetylation and methionine oxidation. The second polypeptide identification setting: enable; the specific restriction setting: unspecific; the polypeptide identification FDR (false discovery rate) setting: 1%, without setting protein identification FDR; the sequence matching length limit setting: 8 to 15 aa; the maximum polypeptide mass setting: 1500 Da, and the maximum charge state setting: 3. The initial allowable mass deviation of leading ions was set to 6 ppm, and the maximum fragment mass deviation was set to 20 ppm. The "match between runs" was set to initiate. The identification result output was saved in the "peptide.txt" file, and the polypeptides matched to the reverse library and the contamination library were removed, and the rest were the identification results of MHC-I restricted epitopes.

Experimental results indicate that the mutant polypeptide, the variant polypeptides and the respective derivative peptide sequences can all be expressed and presented on the HLA molecules on the cell surface. As an example, the mass spectrum of the mutant polypeptide set forth in SEQ ID NO: 2 is shown in FIG. 1, and the results indicate that the above polypeptide can be expressed and presented on the HLA molecules on the cell surface.

Example 3 Verification of Affinity of Polypeptide with T2 Cells

T2 cells are a necessary antigen polypeptide transporter-deficient cell line in the endogenous antigen presentation pathway, and can be used to study the strength of the mutual recognition with MHC molecules in the antigen presentation process.

In order to verify the affinity of exogenous polypeptides with T2 cells, a polypeptide that had been confirmed to have strong affinity with T2 cells was used as positive control, and T2 cells without adding polypeptides were used as background control. The binding of exogenous polypeptides to MHC I molecules on the surfaces of T2 cells can increase the expression of MHC I molecules on the surfaces of T2 cells, and the more stable the binding is, the more MHC I molecules can be detected, and finally the average fluorescence intensity is used as a detection index, and the fluorescence index (FI) is used as a measurement index. Based on this, the affinity of the polypeptide with T2 cells is determined. The higher the FI value, the stronger the affinity of the polypeptide with T2 cells, which is conducive to the subsequent recognition of specific CD8$^+$ T cells.

The synthesized polypeptides were added to 2*10$^5$ T2 cells, and human β2 micro-globulin (with a final concentration of 3 μg/ml) was added and cultivated in 24-well plate. The plate was cultured in an incubator (37° C., 5% CO$_2$) overnight. T2 cells without adding polypeptides were used as background controls, and a CMV polypeptide having a sequence of NLVPMVATV (SEQ ID NO: 9), which is a viral peptide and is also a known polypeptide with strong affinity with T2 cells, was used as a positive control, duplicate wells for each experiment, and the average value was calculated.

Figure 2:
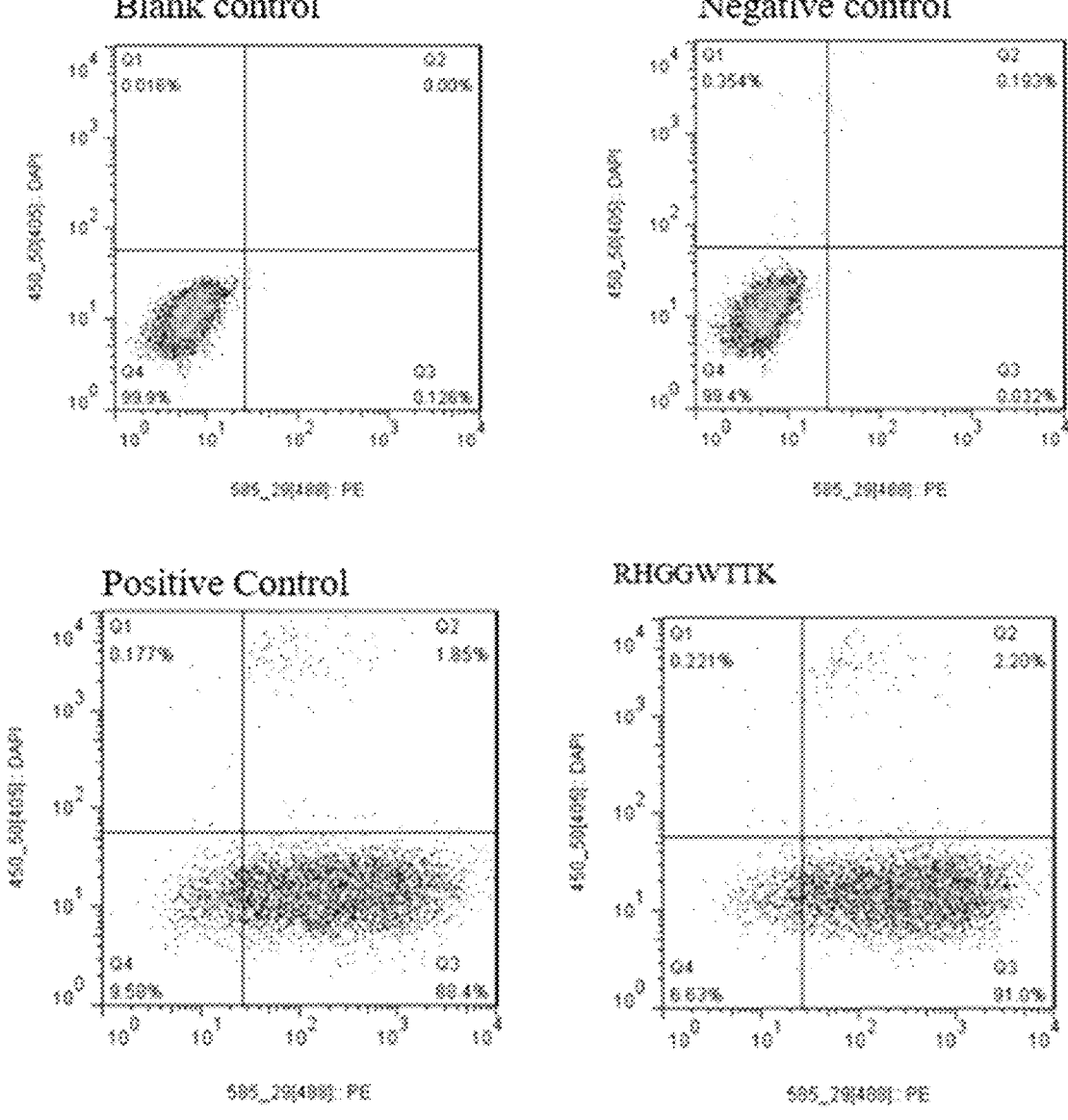
FIG. 2 illustrates result diagrams of flow cytometry verification of affinities of a mutant polypeptide (SEQ ID NO: 2) with T2 cells according to embodiments of the present disclosure.

200 g of cultured cells was centrifuged for 5 minutes to collect the cells. After washing twice with PBS, the cells were directly incubated with FITC-labeled monoclonal antibody against the corresponding HLA typing (HLA-A*11: 01), and maintained at 4° C. for 30 minutes. The mean fluorescence intensity was then detected and analyzed by a flow cytometer (BD FACSJazz™) and its software, see FIG. 2. The obtained T2 cell affinity results are shown in Table 2 below.

TABLE 2

| T2 cell affinity results | | |
| --- | --- | --- |
| Sequences of polypeptides | FI | Conclusion |
| Positive control | 1.63 | |
| RHGGWTTK (SEQ ID NO: 2) | 2.12 | High affinity |

As can be seen from Table 2, compared with the positive control, the polypeptide RHGGWTTK (SEQ ID NO: 2) provided in the present disclosure showed high affinity.

Example 4 Proliferation of CD$^{8+}$ T Cells Stimulated by Polypeptides In Vitro The peripheral blood mononuclear cells (PBMCs) were collected from the volunteers who were positive for the corresponding subtype of the polypeptide. For 2×10$^7$ PBMCs, mononuclear cells were separated by using the adherent method (adhered for 3 h), and CD8$^+$ T cells were isolated by using CD8 magnetic beads. The adherent mononuclear cells were induced to immature DC cells by using GM-CSF (1000 U/ml) and IL-4 (1000 U/ml). Then, the adherent cells were induced into polypeptide-specific mature DC cells by IFN-gamma (100 U/ml), LPS (10 ng/ml), and the respective polypeptides. The obtained polypeptide-specific mature DC cells were co-cultured with volunteers' CD8$^+$ T cells, and IL-21 was added. After 3 days, IL-2 and IL-7 were supplemented. Thereafter, IL-2 and IL-7 were supplemented on day 5 and day 7, and on day 10, the co-cultured cells were counted, and the subsequent ELISPOTs and LDH were detected.

Example 5 Verification of Activation of CD8+ T Cell Immune Response by Polypeptides with ELISPOT Method The ELISPOT method is an enzyme-linked immunospot assay, which can detect the cytokines secreted by a single cell. In the assay, the culture plate was coated with specific monoclonal antibodies, and then the cells to be detected and antigenic stimulant were added for culture. Under the stimulation of the stimulant, the corresponding cytokines were secreted by the T cells, and the secreted cytokines were captured by the antibodies coated on the culture plate. After washing away the cells, the captured cytokines were bonded to fluorescently labeled secondary antibodies to form spots. That is, the cytokines secreted by the cells in the culture can be captured by the coated antibodies and thus presented in the form of colored enzyme-linked spots, so as to detect and verify the strength of the immune response of the CD8$^+$ T cells activated by the polypeptides.

Figure 3:
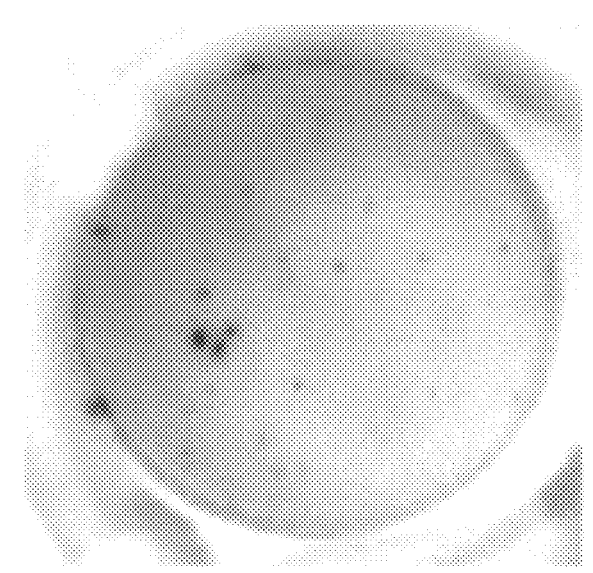
FIG. 3 illustrates in vitro immunogenicity ELISPOT detection result of a mutant polypeptide (SEQ ID NO: 2) according to embodiments of the present disclosure.

With reference to the specification in the ELISPOT kit, the cells cultured in Example 4, T2 cells loaded with testing polypeptide (RHGGWTTK, SEQ ID NO: 2), and T2 cells loaded with irrelevant polypeptide (referring to a polypeptide not stimulating T cells to secrete IFN-gamma interferon and having a specific sequence of LSYRNKPSI, the irrelevant polypeptide used in the following examples also refers to this sequence) were added respectively to the ELISPOT plate for cultivation, and ELISPOTs were detected after 20 hours (see the specification of the ELISPOT kit). The results of ELISPOTs are shown in FIG. 3, and the results are summarized in Table 3 below:

In Table 3, the second row and the third row respectively represent the number of detected spots by using the polypeptide as stimulant and the number of detected spots by using the irrelevant polypeptide as stimulant, and the fourth row indicates a ratio of the number of spots generated by using the polypeptides as stimulant to the number of spots generated by using the irrelevant polypeptide as stimulant. Generally speaking, when the ratio exceeds a certain multiple (>=2), the polypeptide is regarded as having immunogenicity, and the higher the ratio, the stronger the immunogenicity of the polypeptide.

Example 6 Verification of Polypeptide-Specific Killing Activity of CD8$^+$ T Cells By Lactate Dehydrogenase (LDH) Release Assay LDH is an enzyme present in the cytoplasm. LDH will be released into the culture medium when the cell membrane is damaged. Since the released LDH is stable, the measured amount of LDH in the medium can be used as an indicator to measure the number of dead and damaged cells.

The cells cultured in Example 4 were co-cultured with the T2 cells loaded with the testing polypeptide or the irrelevant polypeptide or no polypeptide. In the assay, maximum release wells, volume correction wells, medium control wells, spontaneous release wells, different effect-target ratios (the ratio of the number of T cells to the number of T2 cells) were set, triplicated wells for each group. After 4 hours, 50 µl of the co-cultured cell supernatant was taken and added to 50 µl of LDH substrate mixture, allowing the cell supernatant to catalyze the LDH substrate reaction, finally reading at the wavelength of 490 nm and the reference wavelength of 680 nm. Based on the control wells, the killing activity of target cells killing T2 cells was calculated. The results are shown in Table 4 below. The greater the value shown in Table 4, the stronger the killing effect.

The results indicate that the CD8$^+$ T cells stimulated by these polypeptides have polypeptide-specific killing activity.

TABLE 3

| Polypeptide | Number of spots produced by using testing polypeptide as stimulant | Number of spots produced by using irrelevant polypeptide as stimulant | Multiple (testing/ irrelevant) | Conclusion |
|---|---|---|---|---|
| | Polypeptide stimulating specific CD8 + T cells to secrete IFN-gamma interferon | | | |
| RHGGWTTK (SEQ ID NO: 2) | 104 | 11 | 9 | Having immunogenicity |

TABLE 4

| | T cells specifically recognizing and killing the target cells that present the testing polypeptide | | | | | | | | |
|---|---|---|---|---|---|---|---|---|---|
| Polypeptide | T + T2 + testing polypeptide | | | T + T2 + irrelevant polypeptide | | | T + T2 (loaded with no polypeptide) | | |
| RHGGWTTK    E:T = 10:1 | 0.406 | 0.397 | 0.414 | 0.436 | 0.371 | 0.407 | 0.352 | 0.364 | 0.413 |
| (SEQ ID NO: 2) E:T = 1:1 | 0.324 | 0.324 | 0.351 | 0.278 | 0.293 | 0.308 | 0.279 | 0.298 | 0.322 |

Example 7 Construction of Mouse Subcutaneous Transplanted Tumor Model

This model was used to verify the tumor control effect of the polypeptide pharmaceutical combination, the antigen-presenting cell, and the vaccine proposed by the present disclosure.

1. The encoding gene of each polypeptide was introduced by lentivirus transfection, and the recombinant lentivirus expressing the above-mentioned mutant polypeptide or a variant thereof was constructed and packaged.

2. Construction of human-derived lung cancer cell line expressing the polypeptides The human lung cancer cell line HCC827 was purchased from ATCC (No: CRL-2868), and its HLA subtype was HLA-A*1101 positive. Cells were cultured in DMEM medium containing 10% fetal bovine serum, 100 U/mL penicillin and streptomycin, in an incubator at 37° C., 5% $CO_2$. The packaged lentivirus was transfected into the HCC827 cell line, and antibiotic puromycin was used to continuously screen the surviving HCC827 cell line, and finally the HCC827 cell line expressing the polypeptides was established.

3. NOD SCID mouse human immune reconstitution 600 ml to 900 ml of anticoagulated peripheral blood from healthy volunteers was collected. The PBMCs were separated by Ficoll, and collected for use. 300 NOD SCID mice, in which the immune leakage was excluded, were each intraperitoneally injected with PBMCs ($2*10^7$ cells/0.5 ml) to carry out human immune reconstitution for NOD SCID mice. After 4 weeks, the mice were selected to be inoculated with a human lung cancer cell line model.

4. Construction of human lung cancer tumor model

The established human lung cancer cell line was cultured in DMEM medium containing 10% fetal bovine serum, 100 U/mL penicillin and streptomycin, in an incubator at 37° C., 5% $CO_2$. Tumor cells were collected, centrifuged at 3000 rpm, and washed 3 times with sterile saline. The cells were appropriately diluted, and 40 μl of cell suspension was taken and added to 10 μl of 0.4% tryphenol blue for staining and counting by microscopy, to prepare a tumor cell suspension with a concentration of $1*10^8$ cells/ml. NOD/SCID mice after immune reconstitution were selected and each subcutaneously inoculated with 100 ml of tumor cell suspension. After the inoculation was completed, the inoculation site was observed every day to determine whether infection occurred and whether the tumor regressed naturally after growth. After 7 days, a tumor with a size of about a rice grain under the skin of the mouse can be palpated. The subcutaneous tumor model NOD/SCID mice with immune reconstitution for 4 weeks were treated with DC vaccine, and the tumor volumes were recorded every 3 to 4 days.

Example 8 Schemes of Preparation and Treatment of Polypeptide Vaccine

The HCC827 subcutaneous tumor model NOD/SCID mice with immune reconstitution for 4 weeks were ran-domly divided into 4 groups: an adjuvant+wild-type polypeptide group (in which the wild-type polypeptide is HHGGWTTK (SEQ ID NO: 10)), an adjuvant+blank polypeptide group (i.e., only adjuvant), an adjuvant+mutant polypeptide group (in which the mutant polypeptide is RHGGWTTK (SEQ ID NO: 2)), and an adjuvant+variant polypeptide group (which can be further divided into three groups depending upon the used variant polypeptides, i.e., RAGGWTTK (SEQ ID NO: 1), RSGGWTTK (SEQ ID NO: 3), and RVGGWTTK (SEQ ID NO: 4)), each group including 6 mice. The adjuvant used was Freund's adjuvant.

Figure 4:
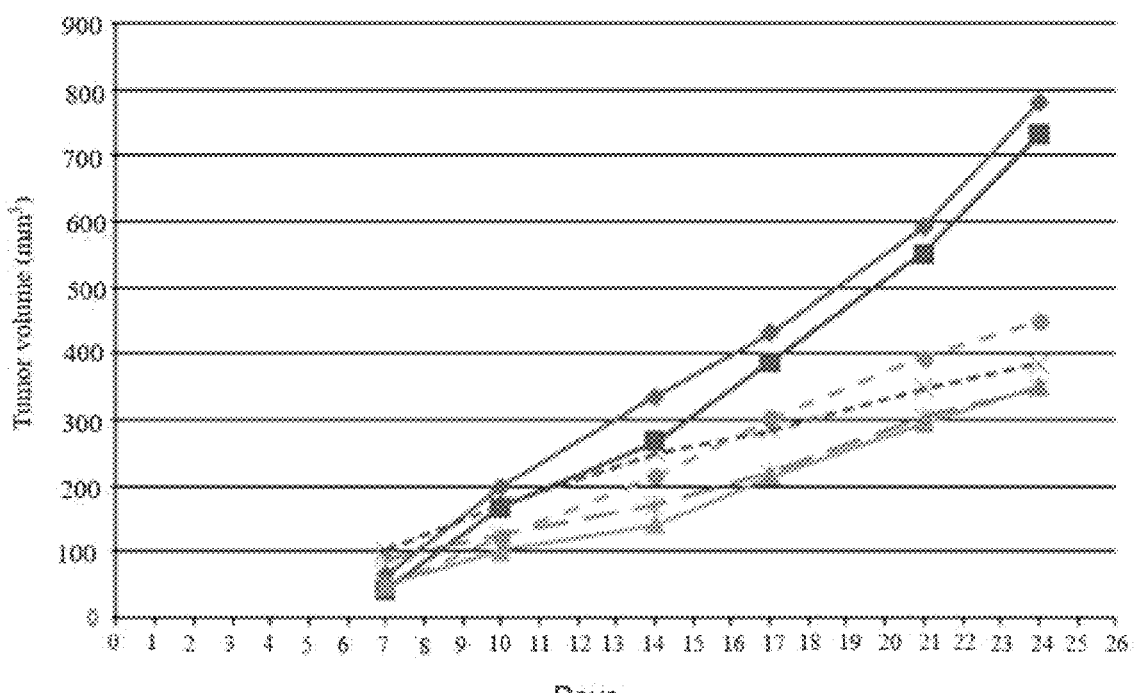
FIG. 4 illustrates a result graph of inhibition of mouse tumor growth by polypeptide vaccines according to embodiments of the present disclosure, where the wild-type polypeptide is as set forth in SEQ ID NO: 10, the mutant polypeptide in SEQ ID NO: 2, the variant polypeptides in SEQ ID NO: 1, SEQ ID NO: 3, and SEQ ID NO: 4.

The first immunization dosage of the polypeptide of each group was 100 ml per mouse. The above polypeptide was resuspended in PBS, mixed with Freund's complete adjuvant (150 ml per mouse), adjusted with PBS to 300 ml per mouse, and subcutaneously injected on the back at two points. After 2 weeks, the same dosage was used for booster immunization (Freund's complete adjuvant was used for the first immunization, and Freund's incomplete adjuvant was used for all subsequent immunizations), for a total of 4 times of immunizations. After the injection, the vital signs of the mice were observed, and the vertical and horizontal sizes of the tumor were measured with a vernier caliper every 3 to 4 days. The tumor volume was calculated in accordance with: tumor volume=½*length*width$^2$. At the same time, the changes in the body weight of the mice were recorded. The results are shown in FIG. 4.

The results indicate that, compared with the wild-type polypeptide-loaded polypeptide vaccine group and the adjuvant group, the mutant polypeptide-loaded vaccine group or the variant polypeptide-loaded vaccine group can significantly slow down the mouse tumor growth.

Figure 5:
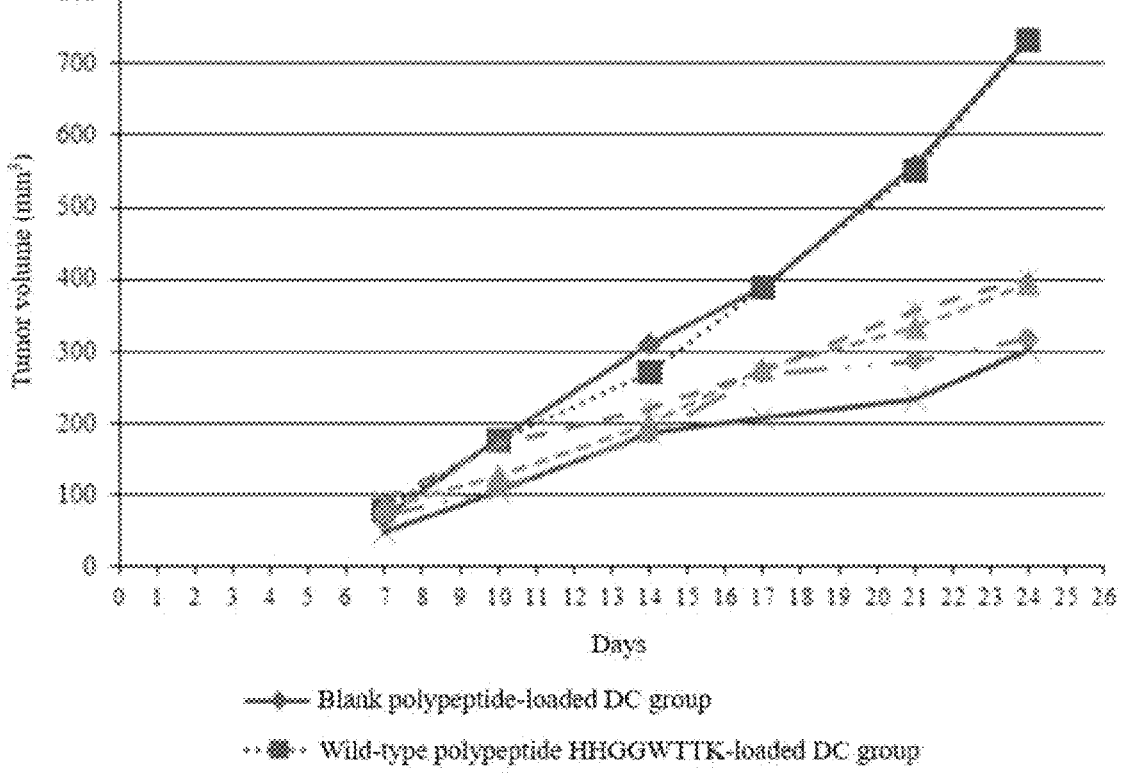
FIG. 5 illustrates a result graph of inhibition of mouse tumor growth by polypeptide DC vaccines according to embodiments of the present disclosure, where the wild-type polypeptide is as set forth in SEQ ID NO: 10, the mutant polypeptide in SEQ ID NO: 2, the variant polypeptides in SEQ ID NO: 1, SEQ ID NO: 3, and SEQ ID NO: 4.

Example 9 Schemes of Preparation and Treatment of DC Polypeptide Vaccine 100 ml to 150 ml of anticoagulated peripheral blood from healthy volunteers was collected. The PBMCs were separated by Ficoll, and collected. The PBMCs were resuspended in RPMI 1640 medium at 2 to $3*10^6$ cells/ml and incubated at 37° C. for 2 h. The adherent cells were DC cells, while the non-adherent cells, i.e., the peripheral blood lymphocytes (PBLs), were sucked and collected for use. The adherent mononuclear cells were induced to immature DC cells by using GM-CSF (1000 U/ml) and IL-4 (1000 U/ml). Then, IFN-gamma (100 U/ml) and CD40L (10 ng/ml) were added, and finally, the wild-type polypeptide combination and the mutant polypeptide combination (with a concentration of 10 micrograms/ml) were added respectively to induce the adherent cells to the mature DC cells. The mature DC cells were harvested and washed 3 times with normal saline. The DC cells loaded with polypeptide were adjusted with normal saline to a concentration of $(4.0±0.5)*10^7$ cells/ml for subsequent experiments. The mice were randomly divided into 4 groups: a wild-type polypeptide-loaded DC group, a mutant polypeptide-loaded DC group, a variant polypeptide-loaded DC group, and a blank polypeptide-loaded DC group, each group containing 6 mice. The cell suspensions for the wild-type polypeptide-loaded DC group, the mutant polypeptide-loaded DC group, the variant polypeptide-loaded DC group, and the blank polypeptide-loaded DC group were prepared. The mice were injected intradermally at the inner thighs near the groin, with 0.1 ml of the suspension per thigh, injected once a week. The dosage was $(4.0\pm0.5)*10^6$ cells/time, 2 injections in total. After the injections, the vital signs of the mice were observed, and the vertical and horizontal sizes of the tumor were measured with a vernier caliper every 3 to 4 days. The tumor volume was calculated in accordance with: tumor volume=½*length*width$^2$. At the same time, the changes in the body weight of the mice were recorded. The results are shown in FIG. 5.

The results indicate that, compared with the wild-type polypeptide-loaded DC vaccine group and the blank polypeptide-loaded DC vaccine group, the mutant polypeptide-loaded DC vaccine group or the variant polypeptide-loaded DC vaccine group can significantly slow down the mouse tumor growth.

Figure 6:
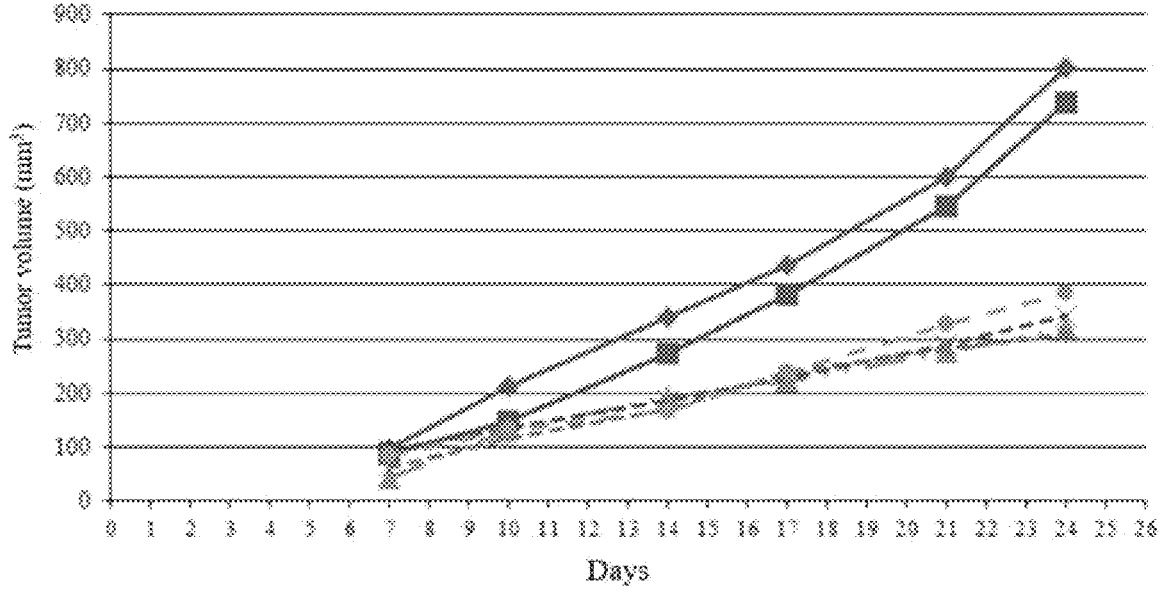
FIG. 6 illustrates a result graph of inhibition of mouse tumor growth by a DC-CTL vaccines according to embodiments of the present disclosure, where the wild-type polypeptide is as set forth in SEQ ID NO: 10, the mutant polypeptide in SEQ ID NO: 2, the variant polypeptides in SEQ ID NO: 1, SEQ ID NO: 3, and SEQ ID NO: 4.

Example 10 Schemes of Preparation and Treatment of Polypeptide-Specific DC-CTL Vaccine The PBLs collected in Example 9 were sorted by magnetic beads to obtain CD8$^+$ T cells. The CD8$^+$ T cells were co-incubated and sensitized with DC cells loaded with the blank polypeptide, DC cells loaded with the wild-type polypeptide, DC cells loaded with the mutant polypeptide, and DC cells loaded with the variant polypeptide, at a cell ratio of DC cells:CD8$^+$ T cells=1:4. The culture medium was incubated with 500 IU/ml IL-2 and 50 ng/ml IL-7, in an incubator at 37° C. with 5% $CO_2$, and the cells were counted after 1 week of culture. In the second week, a second round of stimulation was performed with the DC cells loaded with the blank polypeptide, the DC cells loaded with the wild-type polypeptide, the DC cells loaded with the mutant polypeptide, and the DC cells loaded with the variant polypeptide. A total of three rounds of stimulation was performed, and the medium was appropriately added during the culture. On day 0, day 7, day 14 and day 21 of the culture, the number of lymphocytes was counted, and the cell proliferation index (PI) was calculated, where PI=the number of cells after proliferation/number of inoculated cells. Cytotoxic Tlymphocytes (CTLs) were harvested after 21 days of culture. The cells were resuspended with normal saline, the resuspended volume was 0.2 ml, and the cells were reinfused through the tail vein. The number of cells reinfused in each tumor model mouse was about $1*10^8$ cells. After the injection, the vital signs of the mice were observed, and the vertical and horizontal sizes of the tumor were measured with a vernier caliper every 3 to 4 days. The tumor volume was calculated in accordance with: tumor volume=½*length*width$^2$. At the same time, the changes in the body weight of the mice were recorded. The results are shown in FIG. 6.

The results indicate that, compared with the blank polypeptide control group and the wild-type polypeptide group, the mutant polypeptide or variant polypeptide-activated DC-CTL vaccine can significantly slow down the mouse tumor growth.

In this specification, description reference to the terms "one embodiment", "some embodiments", "example", "specific example", or "some examples" or the like mean that the specific features, structures, materials, or characteristics of the present disclosure described in conjunction with the embodiment or example are included in at least one embodiment or example of the present disclosure. In this specification, schematic representations of the above terms are not necessarily directed to the same embodiment or example. Furthermore, the particular features, structures, materials or characteristics as described may be combined in any suitable manner in any one or more embodiments or examples. Furthermore, those skilled in the art may combine different embodiments or examples described in this specification as well as the features of the different embodiments or examples, as long as they are not contradictory.

Although the embodiments of the present disclosure have been illustrated and described above, it should be understood that the above-mentioned embodiments are exemplary and shall not be construed as limitations to the present disclosure. Those skilled in the art can make variations, modifications, substitutions, and alterations to the above-described embodiments within the scope of the present disclosure.

---

What is claimed is:

1. A construct, comprising:
   an isolated nucleic acid, encoding a polypeptide in an isolated polypeptide group; and
   a control sequence, operably linked to the nucleic acid, wherein the isolated polypeptide group comprises a first peptide group;
   wherein the first peptide group is selected from the group consisting of polypeptides having the amino acid sequences of SEQ ID NO: 1, SEQ ID NO: 3, SEQ ID NO: 4, and combinations thereof.

2. An expression vector, comprising the construct according to claim 1.

3. A host cell, carrying the construct according to claim 1.

4. The construct according to claim 1, wherein the isolated polypeptide group further comprises a second peptide group, wherein the second peptide group is selected from the group consisting of derivative polypeptides, each of the derivative polypeptides comprising a front peptide segment, a middle peptide segment, and a back peptide segment that are connected in sequence, wherein the middle peptide has at least 80% homology with the amino acid sequence of SEQ ID NO: 1, SEQ ID NO: 3 or SEQ ID NO: 4, and wherein a sum of lengths of the front peptide segment and the back peptide segment ranges from 17 amino acids to 19 amino acids.

5. The construct according to claim 4, wherein the middle peptide segment comprises the amino acid sequence of SEQ ID NO: 1, SEQ ID NO: 3, or SEQ ID NO: 4.

6. The construct according to claim 4, wherein the derivative polypeptide is selected from the group consisting of SEQ ID NO: 5, SEQ ID NO: 6, SEQ ID NO: 7, SEQ ID NO: 8, and combinations thereof.

7. The construct according to claim 1, wherein the isolated polypeptide group is at least one group of:
   group 1: at least two polypeptides consisting of SEQ ID NO: 1, SEQ ID NO: 3, and/or SEQ ID NO: 4; and/or
   group 2: at least one polypeptide consisting of SEQ ID NO: 1, SEQ ID NO: 3, and/or SEQ ID NO: 4 and at least one polypeptide consisting of SEQ ID NO: 5, SEQ ID NO: 6, SEQ ID NO: 7, and/or SEQ ID NO: 8.

8. A pharmaceutical composition, comprising:
   a polypeptide in the isolated polypeptide group encoded by the nucleic acid of the construct according to claim 1; and
   a pharmaceutically acceptable excipient.

9. A tumor vaccine, comprising a polypeptide in the isolated polypeptide group encoded by the nucleic acid of the construct according to claim 1.

10. A tumor vaccine, comprising the host cell according to claim 3.

11. A method for treating a patient suffering from tumors, comprising:
   administering an effective amount of the pharmaceutical composition according to claim 8 to the patient.

12. A method for treating a patient suffering from tumors, comprising:

administering an effective amount of the tumor vaccine according to claim 9 to the patient.

\* \* \* \* \*